United States Patent [19]

Dorband et al.

[11] Patent Number: 4,976,909
[45] Date of Patent: Dec. 11, 1990

[54] METHOD FOR MANUFACTURE OF SURGICAL FASTENING DEVICE

[75] Inventors: Glen C. Dorband, South Bound Brook; Alfred Liland, Wharton; Edgar Menezes, Somerville; Peter Steinheuser, Manville; Nicholas M. Popadiuk, Raritan; Stephen J. Failla, Chester, all of N.J.

[73] Assignee: Ethicon, Inc., Somerville, N.J.

[21] Appl. No.: 12,539

[22] Filed: Feb. 9, 1987

Related U.S. Application Data

[62] Division of Ser. No. 733,351, May 13, 1985, Pat. No. 4,671,280.

[51] Int. Cl.$^5$ .............................................. B29C 71/00
[52] U.S. Cl. ..................................... 264/235; 264/346; 606/220
[58] Field of Search .................... 264/235, 346, 331.21, 264/280, 285, 320; 128/335.5

[56] References Cited

U.S. PATENT DOCUMENTS

| | | | |
|---|---|---|---|
| 3,839,297 | 10/1974 | Wasserman et al. | 128/335.5 |
| 4,052,988 | 10/1977 | Doddi et al. | 128/335.5 |
| 4,333,903 | 6/1982 | Yoshida et al. | 264/346 |
| 4,591,630 | 5/1986 | Gertzman et al. | 264/346 |
| 4,646,741 | 3/1987 | Smith | 128/335.5 |

Primary Examiner—Jay H. Woo
Assistant Examiner—C. Scott Bushey

[57] ABSTRACT

A tissue fastening device comprising (a) a fastener member having a pair of legs extending from the same side of a connecting cross piece, said fastener member adapted to be placed on one side of the tissue to be joined with the legs penetrating the tissue, said fastener member being an oriented crystalline polymeric material, whereby the fastener member has sufficient inherent strength and stiffness so said legs can penetrate the tissue to be fastened, and (b) a receiver member to secure said fastener member in place. The fastener member is formed by forming an oriented polymeric filament into the configuration of the fastener member, and annealing the filament while in such configuration while it is being restrained so as to prevent shrinkage.

7 Claims, 5 Drawing Sheets

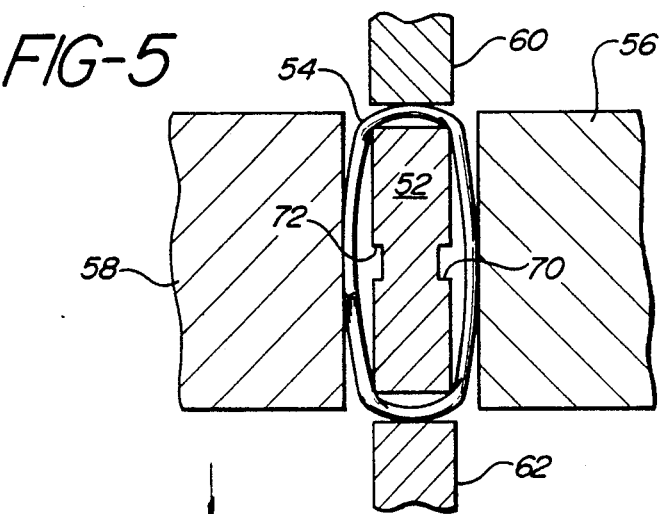
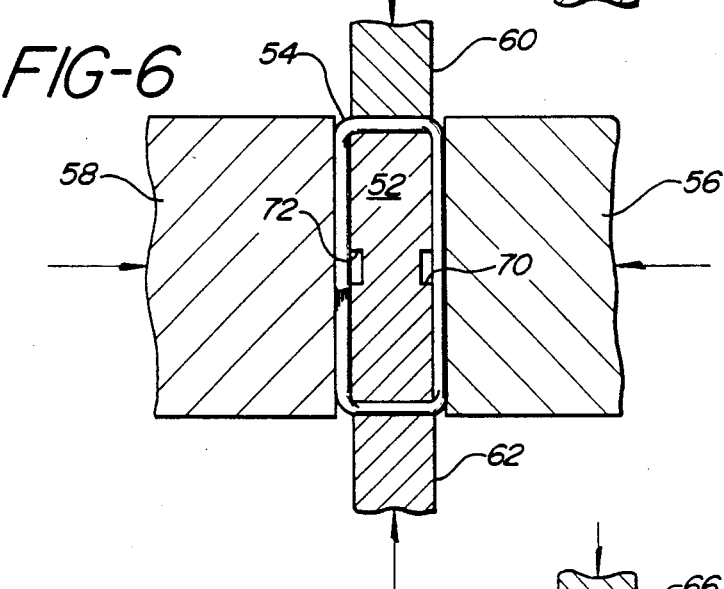
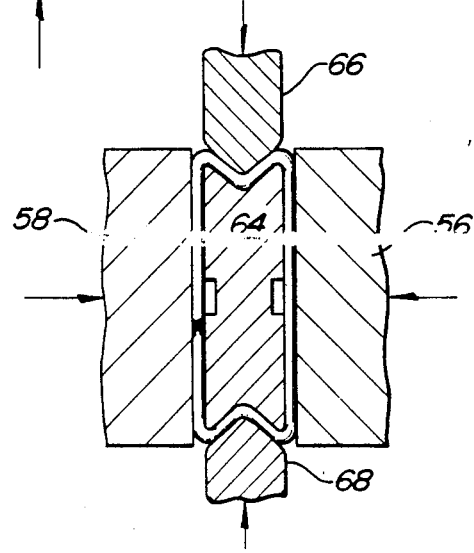

METHOD FOR MANUFACTURE OF SURGICAL FASTENING DEVICE

This is a division of application Ser. No. 733,351, filed May 13, 1985, Pat. No. 4671280.

BACKGROUND OF THE INVENTION

In most surgical procedures, one or more of the steps in the procedure is the fastening of tissue. Not only does skin tissue require fastening, but fastening of various organ tissues, fascia tissue, muscle tissue, and other types of tissue may be required. Until the recent past, fastening of tissue has been accomplished almost entirely with sutures. In an effort to reduce the time required in the tissue fastening steps, the surgical profession has begun to replace sutures with metallic staples.

The metallic fasteners are slowly being accepted by the medical and surgical community. However, metallic fasteners do suffer from certain disadvantages; for example, they are foreign bodies which the body must cope with during recuperation after the surgical procedure. Furthermore, metallic staples and fasteners may disrupt and interfere with various subsequent diagnostic imaging techniques, such as x-ray, computerized axial tomography, or magnetic resonance imaging.

Polymeric tissue fastening devices, especially such devices which are absorbable by the body, show promise of eliminating these disadvantages of the metallic fastener. Devices of this nature are described in U.S. Pat. Nos. 4,060,089, 4,402,445, 4,317,451, and 4,428,376. Though the desirability of producing such fastening devices from polymeric materials, especially from absorbable polymeric materials, has been well known, as suggested in the above-mentioned patents, these devices have been slow to commercialize because it has been difficult to develop a fastener that is sterilizable, non-toxic, and has the mechanical properties required to be able to penetrate tissue without having complicated guiding and support devices to aid in that penetration, and to also maintain the tissue closed or fastened for a sufficient period of time to allow for the requisite healing of tissue, to then be absorbed within a reasonable period of time, and to do all of this with an article of minimum bulk.

It is an object of this invention to produce a fastening device that will not disrupt subsequent diagnostic procedures. It is also an object of this invention to produce a non-toxic, sterilizable, polymeric tissue fastening device that readily penetrates tissue. It is yet a further object of the invention to produce such a minimum bulk device that, once it has been placed to fasten tissue together, will maintain its strength for a sufficient period of time to allow for the healing of that tissue, and to then be absorbed by the body. These and other objects of the invention will be more fully appreciated from the following description.

SUMMARY OF THE INVENTION

The invention provides a non-toxic, sterilizable, polymeric tissue fastening device which comprises a fastener member having a pair of legs extending from the same side of a connecting cross piece. The fastener member is adapted to be placed on one side of the tissue to be joined. The legs of this fastener member have sufficient strength to penetrate tissue by appropriately pressing the fastener member to force the legs through the tissue. A receiver member is placed on the opposite side of the tissue to be joined and engaged with the legs to secure the device in place.

In a preferred embodiment of the invention, the receiver member is made from deformable material and configured to provide an interference or friction fit with the legs of the fastener member to lock the two members together.

The fastener member is an oriented crystalline polymeric material, and in a preferred embodiment of the invention, the polymeric material is absorbable by the body. The fastener member is crystalline and appropriately oriented to ensure sufficient strength to allow the legs to penetrate the tissue in the absence of assisting members. Orientation also enhances the ability of the fastener member to retain its strength in vivo, and therefore the fastener members and receiver member of the invention maintain a sufficient portion of their strength properties over desirable lengths of time to maintain the tissue in a joined position and allow for adequate healing and mutual joining of the tissue. Crystallinity enhances the ability of the fastener member to withstand elevated temperatures during processing and storage, e.g., temperatures up to about 140°F., and still retain dimensional stability.

The fastener members of the invention are produced from oriented filaments of the desired polymer. The oriented filament is formed into the desired staple configuration and then annealed, without shrinkage, at a temperature between the glass transition temperature and the melting temperature of the polymer.

The annealed and shaped fastener member may then be further shaped to size the leg portions, form sharpened points on the legs, and the like.

BRIEF DESCRIPTION OF THE DRAWINGS

The invention will be more fully described in conjunction with the accompanying drawings wherein:

FIG. 5 is a cross-sectional view taken along line 5—5 of FIG. 4, prior to annealing;

FIG. 6 is a view similar to FIG. 5, after annealing;

FIG. 11 is a view similar to FIG. 6 showing an alternative embodiment of the inventions.

DETAILED DESCRIPTION OF THE INVENTION

Figure 1:
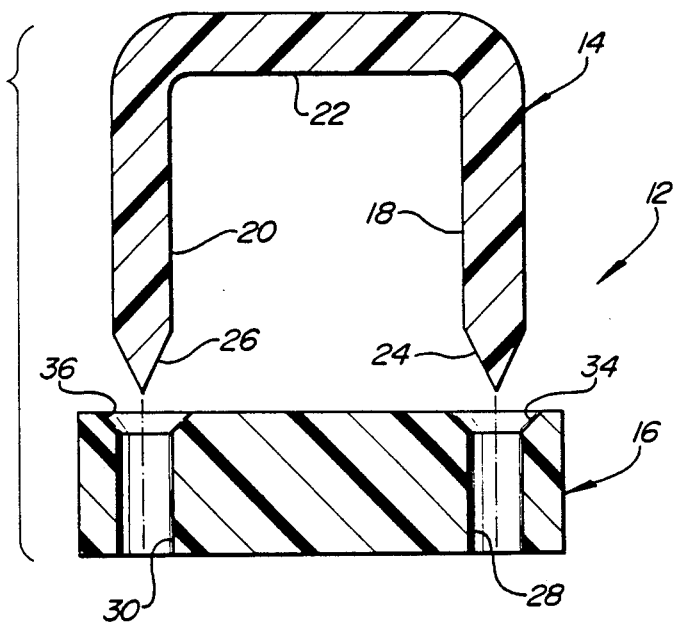
FIG. 1 is a cross-sectional elevation of one embodiment of the fastener member and receiver member of the invention.

Referring to the drawings, in FIG. 1 there is shown a fastener 12 of the invention. The fastener 12 comprises a fastener member 14 and a receiver member 16. The fastener member 14 comprises a pair of legs 18 and 20 which are substantially parallel in this embodiment and which are connected by a cross member 22. The free ends 24, 26 of the legs have been pointed to assist in the penetration of tissue. (In the context of this invention, "penetration" of tissue occurs not only when the legs of the fastener pass through tissue by piercing the tissue, but also in those cases in which the tissue is not pierced but rather is attenuated and pushed ahead of the legs and surrounds the legs, even when the legs have been secured in the receiver).

The receiver 16 is a polymeric piece with a pair of openings 28, 30 disposed to accept the legs 18, 20. The openings are sized to be just smaller in diameter than the diameter of the legs to produce a tight interference fit between the opening and the leg to hold the two pieces together when in use. To illustrate, when the openings 28, 30 have diameters d of from about 0.02 to about 0.03 inch, if the legs 18, 20 have diameters about 0.002 to 0.003 inch larger, then satisfactory strength is obtained in the assembled fastener. In the version shown, the openings 28, 30 are beveled or countersunk at the top, as shown at 34, 36, to assist in guiding the legs 18, 20 into the openings 28, 30 as the legs penetrate tissue.

Figure 2:
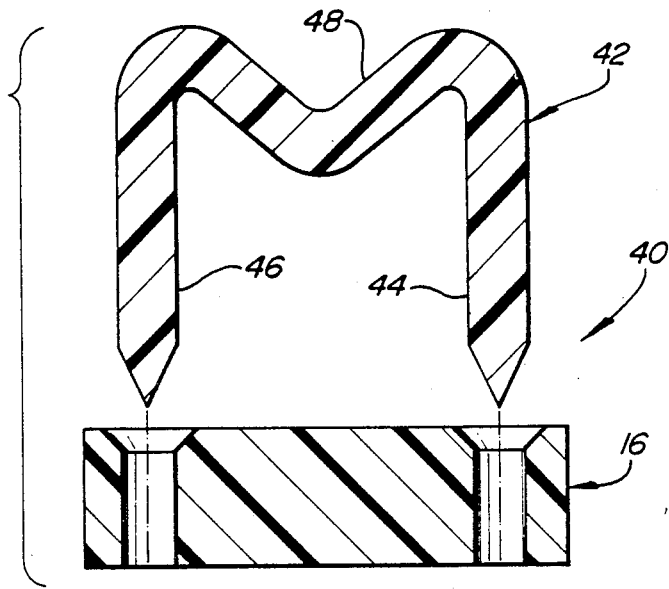
FIG. 2 is a cross-sectional elevation of another embodiment of the fastener member and receiver member of the invention.
Figure 3:
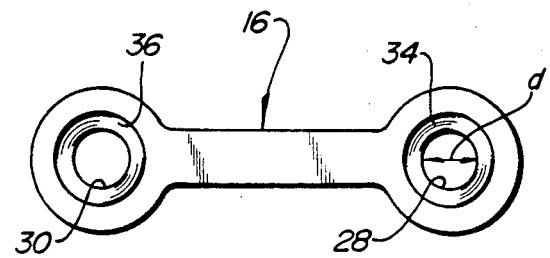
FIG. 3 is a top plan view of the receiver member shown in FIGS. 1 and 2.

In FIG. 2 there is shown another embodiment of a fastener according to the invention. Again, the fastener 40 comprises a fastener member 42 and a receiver member 16. The fastener member comprises a pair of legs 44 and 46 connected by a cross piece 48. In this embodiment, the fastener member 42 has an "M" configuration. The receiver 16 is identical to the embodiment shown in FIGS. 1 and 3.

It should be appreciated that the shape of the fastener member may be varied depending upon the type of tissue to be joined. Also, the cross sectional shape of the fastener member, especially the leg portions, may be modified. Circular cross sections have been described in conjunction with FIGS. 1 and 2; however, oval, square, rectangular, or other cross-sectional shapes may be used. As described with regard to the figures, the fastener members have tapered sharpened points. Again, various types of tapering or points may be used, depending primarily upon the tissue the fastener member is meant to penetrate. Preferably, the point is symmetrical around the longitudinal axis of the leg to avoid setting up lateral forces that would tend to deflect the leg off course as it is penetrating tissue.

The fastener members used in the invention are oriented and crystalline. What is important is that the polymer in the fastener member be oriented to a sufficient degree to provide the necessary strength and stiffness to allow the fastener member to be placed and allow the leg to penetrate tissue without having to use auxiliary equipment to support the leg while passing it through the tissue to be joined. The use of auxiliary equipment increases the trauma caused on the tissue when placing the fastener, and increases the complexity of the instrument. Also, when the fasteners are made from absorbable polymers, orientation and crystallinity are required to provide the fastener member with sufficient strength for a sufficient period of time to maintain the tissue in the desired joined configuration for the time required to allow for healing of the tissue before the fastener loses its strength and is ultimately totally absorbed.

The fastener members and receivers of the invention may be made from non-absorbable bio-compatible polymeric materials such as polypropylene, polyethylene, nylon, polyester, etc. It is preferred that the fastener members and the receivers be made from absorbable polymeric materials such as the polymers and copolymers of lactide and glycolide, etc. Some of the reasons for this are (a) the absorbable polymers are ultimately totally absorbed by the body and alleviate the problems the human body has in coping with foreign objects within the body; and (b) such materials also have no disruptive effect on subsequent diagnostic procedures. It is preferred that the fastener members be made from the crystalline polymers and copolymers of lactide and glycolide. These polymeric materials may be oriented sufficiently to provide the desired physical properties in the fastener member while also providing the desired absorption characteristics.

It is preferred that the receivers be made from the polydioxanone polymers, especially poly(p-dioxanone) homopolymer, including blends of these polymers with other absorbable polymers. These polymers provide the desired strength, flexibility and deformability in the receiver to provide excellent securing characteristics between the receiver and the fastener leg.

The fastener member has certain minimum functional strength requirements. It must be possible to drive the legs through the tissue to be fastened and have the legs hold their course so that they will enter the openings in the receiver. To this end, the legs will usually have a Young's modulus of at least about $2 \times 10^5$ psi and preferably at least about $1 \times 10^6$ psi, up to about $3 \times 10^6$ psi. The Young's modulus is determined by an Instron tensile tester using a 5-inch gauge length, a chart speed of 20 inches per minute, and a crosshead speed of 5 inches per minute.

The properties of the fastener and receiver must be such that when the two parts are mated they hold together securely so as to hold the tissue together for the critical wound healing period. A friction or interference fit between the fastener and receiver is best achieved when the polymeric material from which the receiver is made is more compliant than the material from which the fastener member is made. Young's modulus is related to compliance, so a convenient way to determine whether or not a pair of polymers can be used as the fastener and receiver is to compare their Young's modulus values. The polymer from which the receiver is made will usually have a significantly lower Young's modulus value than the polymer used for the fastener member.

The fastener members used in the invention are made by forming an extruded oriented filament of the desired polymer into the configuration of the fastener member, and then annealing the formed filament at a temperature between the glass transition temperature and the melting temperature of the polymer. The annealing is carried out with the formed filament under restraint so as to prevent shrinkage of the filament, and so as to maintain the orientation of the filament and to keep the filament in the desired fastener member configuration.

Figure 4:
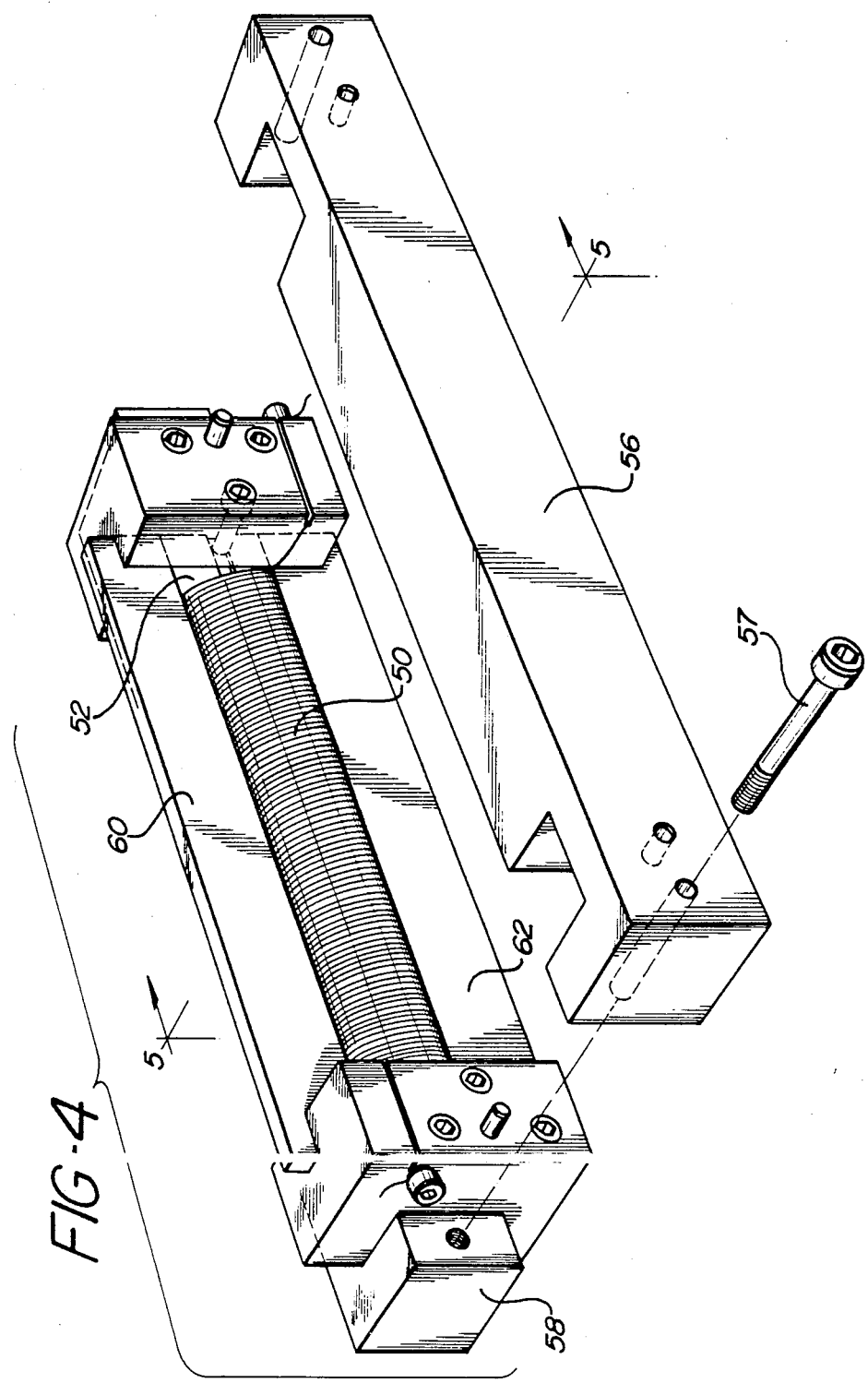
FIG. 4 is a perspective view of an arrangement of apparatus that can be used in carrying out the process of the invention.

This procedure is illustrated by the following description of a specific process for making fastener members from oriented filaments of an absorbable polymer of 90 mol per cent glycolide and 10 mol per cent lactide:

Referring to FIGS. 4-6, extruded oriented filament 50 (made by extrusion and orientation procedures that are analogous to those that are known in the art) is wound tightly around a forming bar 52. Preferably, each individual coil 54 or loop of the wound filament 50 is touching the adjacent coil 54 or loop, as is shown in FIG. 4. The filament 50 is wound around the forming bar 52 under sufficient tension to eliminate any slack in the wound filament. Hand winding with a tension of from about 1 to about 2 pounds has been found to be satisfactory with the polymer under consideration.

The winding of the filament 50 around the forming bar 52 is carried out at a temperature below the glass transition temperature of the polymer. Ordinarily, winding will be done at ambient temperature. Because the oriented filament is quite stiff, the coils 54 are bowed out slightly from the sides of the forming bar 52, as is seen most clearly in FIG. 5. Thus, the coils 54 do not fully assume the desired fastener member (or "staple") configuration until the filaments are heated, which will normally be during the annealing step.

After the filament 50 is wound around the forming bar 52, the wound bar is enclosed in clamps, shown as 56, 58, 60, and 62 in FIGS. 4-6. The clamps are used to precisely fix the outer dimensions of the fastener member to ensure proper fit in the applying instrument. The clamps are tightened against stops (not shown) such that the stopped gap between the clamps and the forming bar is slightly less than the diameter of the oriented filament. To illustrate the order of magnitude contemplated, with an oriented filament having a diameter of 0.030 inch, the stopped gap between the bar 52 and each clamp 56, 58, 60, 62 would be 0.028 to 0.029 inch. Oriented filaments made from the lactide/ glycolide polymer used for illustration here are so stiff that one cannot hand tighten the clamps down to the stops while the filament is at ambient temperature. Therefore, the final tightening will ordinarily be done when the filaments have been heated above the glass transition temperature. This final tightening may be done by further hand tightening or by the use of a means such as a spring or a pneumatic cylinder to tighten down each clamp to the stopped gap during the annealing step.

Tightening of the side clamps 56, 58 may be effected by tightening bolts, such as that shown as 57, which connect the two side clamps 56, 58 to each other. Tightening of the end clamps 60, 62 may be effected by standard means, such as by enclosing the fixture in a vise (not shown), which tightens against the end clamps 60, 62.

The entire fixture comprising the clamped forming bar can be placed in an oven for annealing at a temperature between the Tg and Tm of the polymer. For the exemplified polymer, an annealing time of about 16 hours at 135°C. under a dry nitrogen atmosphere has been found to be satisfactory. If the final tightening of the clamps down to the steps is to be done by hand, the fixture can be removed from the oven about one-half hour after the annealing step began to carry out this final tightening. The fixture is then placed back in the oven for the remainder of the annealing.

After the annealing, the fixture is cooled down to ambient temperature, e.g., over two hours. After it has cooled down (i.e., after the filament has cooled to below the glass transition temperature of the polymer), the clamps are then removed. The annealed filament on the forming bar will then have the configuration shown in FIG. 6. (If it is desired to produce an "M" shaped fastener member, the forming bar 64 and end clamps 66, 68 are modified as shown in FIG. 11.)

Figure 7:
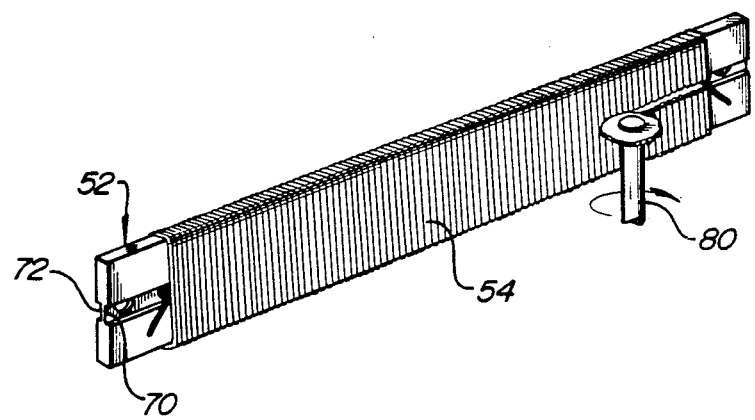
FIG. 7 is a perspective view of oriented filament wound around a forming bar, after annealing, showing the filaments being cut.

After annealing and removing the clamps, the wound filament is cut in half, as shown in FIG. 7, by passing a cutting instrument down the center of cavities formed by the two longitudinal grooves 70, 72 in the forming bar 52. This cut may be made with a rotating saw, shown as 80. This cut then forms two rows of fastener member blanks which require only trimming and forming of the pointed ends of the legs. The blanks can be hot sheared to slightly longer than the desired length, and the points can be added by cutting each point with a rotating cutting edge. The final fastener member then has the staple configuration shown in FIGS. 1 and 2 as 14 or 42.

The forming bar used in the annealing step performs two functions. It acts as a template which, in cooperation with the four clamps, forms the oriented filament into the desired configuration of a staple or fastener member, and it prevents the oriented filament from shrinking, thereby permitting the filament to retain its orientation and, hence, the desirable combination of properties exhibited by the fasteners of this invention.

The forming bar, in cooperation with the clamps, serves to form the oriented filament into the desired configuration of the fastener member. By this configuration is meant two legs extending from the same side of a connecting cross piece, and is intended to include the configuration shown in FIGS. 5-7 wherein, in effect, each formed loop comprises two fastener members connected to each other through one common leg.

The degree of orientation of a polymer is ordinarily measured by birefringence. The birefringence of fastener members made from the oriented 90/10 glycolide/lactide polymer as discussed herein have been found to have a birefringence $\Delta n$ of 0.08. The extruded filament of this material, prior to orientation, had a birefringence $\Delta n$ of 0.0012. A degree of orientation that would yield a birefringence in this material of about 0.005 is about the minimum that would yield a product that would achieve the objects of the invention.

The polymer used in making the fastener member is crystalline as well as oriented. A minimum of about 10 per cent crystallinity, determined by X-ray diffraction, is required. The 90/10 glycolide/lactide polymer described above usually has a crystallinity of about 35 per cent.

The receiver members of the invention may be made by various molding, machining, or stamping techniques, as is known in the art. A preferred technique for making the receivers of the invention is by standard injection molding.

Figure 8:
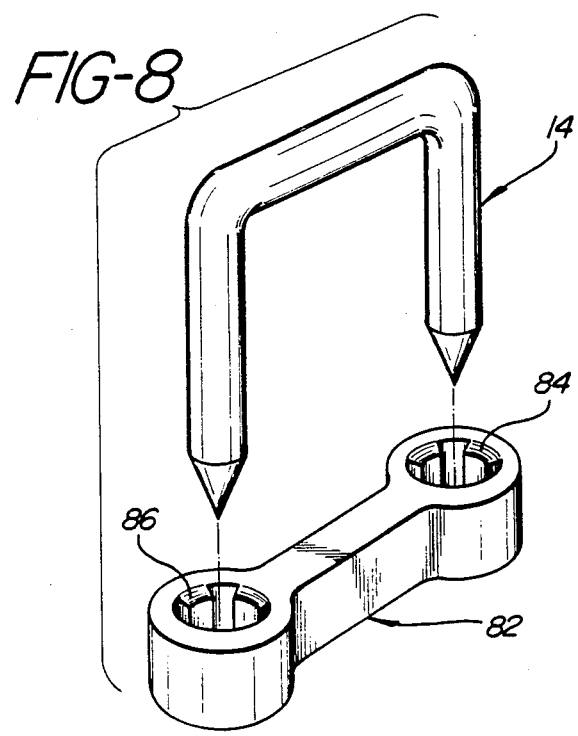
FIG. 8 is a perspective view of the fastener of the invention, showing a preferred embodiment of the receiver member.
Figure 9:
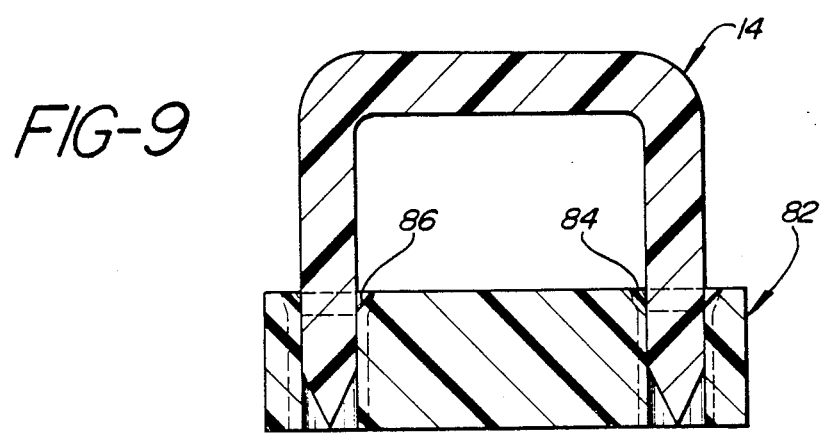
FIG. 9 is a cross-sectional elevation of the embodiment of FIG. 8, showing the receiver member engaging the fastener member.
Figure 10:
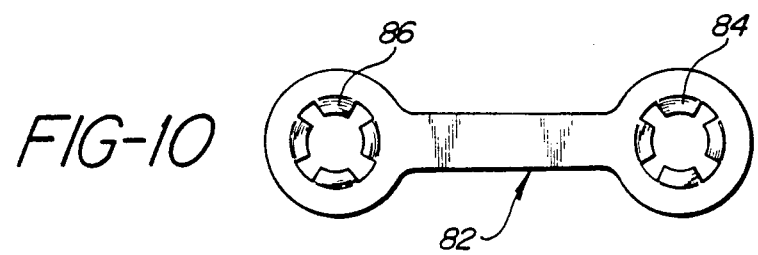
FIG. 10 is a top plan view of the receiver member of FIG. 8.

In the alternative embodiment shown in FIGS. 8-10, the receivers 82 have fluted openings 84, 86. The flutes in the openings reduce the amount of force needed to press the fastener member into the receiver member, and also serve to make this fastening force less sensitive to diminsional variations.

The invention will be more fully described by the following specific example:

EXAMPLE 1

An absorbent polymer made from 90 mol per cent glycolide and 10 mol per cent lactide having an inherent viscosity ("I.V.") of 1.39 dl/gm, tested at a concentration of 0.1 gram/dl in hexafluoroisopropyl alcohol ("HFIP") at 25°C., and a melt index of 0.238 (melt index determined by using a Tinius Olsen Extrusion Plastometer using a die size of 0.026 inch, a temperature of 235°C., and a load of 3.7 kilograms), is extruded into a monofilament. The monofilament has a diameter of 0.08 inch and is extruded using a 1¼ inch single screw extruder through a 0.1 inch diameter orifice. The filament is quenched in a water bath maintained at 77°F. Mineral oil is then coated on the surface of the extruded filament to reduce chattering or scuffing during the orientation. The oil is scoured from the filament at the end of the process. The extruded monofilament is oriented down to a diameter of about 0.0298 inch. The first stage of orientation has a 6.89× draw ratio and the filament is drawn over heated rolls at 60°C. The oriented filament is stored for 24 hours at room temperature under a nitrogen atmosphere prior to the second stage of the orientation process. The second stage of orientation has a 1.07× draw ratio and is carried out by passing the filament through a heated oven at 104°C., with the oven located between two godets that are at ambient temperature. The resulting monofilament has a diameter of 29.8 mils, a tensile strength of about 80 pounds, an elongation of 35%, and a Young's modulus of $1.9 \times 10^6$ psi. This orientation procedure produces a filament having a stress-strain curve that does not possess a yield point.

The oriented monofilament is wound on a forming bar as is shown in FIGS. 4 and 5. The monofilament is wound with about one pound winding tension. The ends of the fiber are tied off at each end of the fixture, and clamps are added as shown in FIGS. 4 and 5. The fixture is annealed in an oven for 16 hours at 135°C. in a nitrogen atmosphere. (The clamps are re-tightened after the first half-hour of the annealing step.) This annealing heat sets the monofilament in the wound configuration. The fixture is removed from the oven and cooled to room temperature for about 2 hours. The monofilament is cut along the longitudinal grooves 70, 72 to produce U-shaped staples. The legs of the staples are cut to point them in a conical point, as shown in FIG. 1.

The receivers are produced from a polydioxanone polymer. They are produced by injection molding. The receivers have the shape depicted in FIGS. 1 and 3.

EXAMPLES 2-5

These examples illustrate typical conditions that can be used to make the extruded and oriented filaments from which the fastener members may be shaped. Table I, below, displays conditions for four polymers, poly(p-dioxanone) and three glycolide ("G")/lactide ("L") copolymers (the proportions are mol %).

The filaments were extruded using a one-inch vertical extruder, quenched in water at ambient temperature, and then drawn in one or two stages, in some cases with an oven between the two godets in the second stage of orientation. Table I also presents typical annealing conditions that can be used for the production of fastener members from these polymers by the procedure taught herein.

Table II, below, displays the diameter, tensile strength, and elongation at break of the filaments.

TABLE I
PROCESS CONDITIONS FOR EXTRUDED STAPLES

| POLYMER Type | Example No. | EXTRUSION Block/Die Temp. (°C.) | EXTRUSION Die Dia./Holes (Mil/#) | ORIENTATION STAGE 1 I Godet Speed/Temp. (fpm/°F.) | ORIENTATION STAGE 1 II Godet Speed/Temp. (fpm/°F.) | ORIENTATION STAGE 1 III Godet Speed/Temp. (fpm/°F.) |
|---|---|---|---|---|---|---|
| (90% G/10% L) | 2 | 246/250 | 100/1 | 19/72 | 19/140 | 132/72 |
| (30% G/70% L) | 3 | 157/154 | 100/1 | 20/110 | 28/130 | 100/72 |
| (15% G/85% L) | 4 | 182/183 | 100/1 | 24/72 | 24/140 | 94/72 |
| Poly(p-dioxanone) | 5 | 119/117 | 120/6 | —/— | —/— | —/— |

| POLMER Type | ORIENTATION STAGE 2 I Godet Speed/Temp. (fpm/°F.) | ORIENTATION STAGE 2 II Godet Speed/Temp. (fpm/°F.) | ORIENTATION STAGE 2 Oven Temp. (°F.) | ORIENTATION STAGE 2 III Godet Speed/Temp. (fpm/°F.) | ANNEALING Time (hrs.) | ANNEALING Temp. (°C.) |
|---|---|---|---|---|---|---|
| (90% G/10% L) | 29/72 | 30/72 | 250 | 31/72 | 16 | 135 |
| (30% G/70% L) | —/— | —/— | —/— | —/— | 5 | 75 |
| (15% G/85% L) | 29/72 | —/— | 128 | 32/72 | 0.5 | 65 |
| Poly(p-dioxanone) | 10/72 | 48/72 | 230 | 61/72 | 6 | 85 |

TABLE II
TENSILE PROPERTIES OF EXTRUDED ORIENTED FILAMENTS

|  | Diameter, (Mils) | Tensile St., (Lbs.) | Elongation, (%) |
|---|---|---|---|
| 2 | 30.3 | 75 | 45 |
| 3 | 30.0 | 71 | 10 |
| 4 | 30.0 | 20.0 | 30 |
| 5 | 20.8 | 26.1 | 60 |

EXAMPLE 6

The fasteners of the invention maintain measurable holding strength in vivo for a period of time sufficient to enable joined tissue to heal. This is illustrated by the fact that in vitro testing in phosphate buffer, pH=7.27, at 37°C., of the fasteners reveals that the force to separate the receiver from the fastener member is still measurable after 21 days, and is usually at least one pound.

The procedure for testing the separation force is the following:

An Instron Tensiometer is set as follows:
Crosshead speed — 0.5 inch/minute
Chart speed — 5.0 inches/minute
Gauge Length — 1.5 inches
Full scale load as follows:

| Time in days | Full Scale Calibrations |
|---|---|
| 0 | 10 pounds |
| 7 | 5 pounds |
| 14 | 5 pounds |
| 21 | 2 pounds |

| Time in days | Full Scale Calibrations |
|---|---|
| 28 | 2 pounds |

The staples (fastener members) are inserted in the receivers, leaving a slight gap to simulate the space taken up by tissue, and are then placed in the phosphate buffer at 37°C. The samples are tested initially and after 7, 14, 21, and 28 days.

The separation force is measured by engaging the cross piece (e.g., part 22 in FIG. 1) of the staple with a tab of an Instron test fixture, and pulling against a strip of polyester film that has been bent around the receiver by passing it through the gap between the staple and receiver. Typical initial separation forces vary from about 5 to 8 pounds, and typical spearation forces after 21 days in phosphate buffer at 37°C. are from 1 to 2 pounds and occasionally up to 3 to 3½ pounds.

We claim:

1. Process for producing a fastener member having a pair of legs extending from the same side of a connecting cross piece, said fastener member being adapted to be placed on one side of tissue to be joined with the legs penetrating the tissue, said fastener member being an oriented crystalline polymeric material, whereby the fastener member has sufficient inherent strength and stiffness so said legs can penetrate the tissue to be fastened, and said fastener member being adapted to mate with a receiver member to secure said fastener member in place, which process comprises forming an oriented polymeric filament into the configuration of said fastener member, annealing the thus formed filament at a temperature between the glass transition and melting temperatures of said polymer while restraining said filament from shrinking, and cooling the filament to a temperature below the glass transition temperature of said polymer while maintaining said filament under such restraint in the said configuration.

2. The process of claim 1 wherein the forming of the oriented polymeric filament into the configuration of the fastener member includes the step of winding said filament around a forming bar having a rectangular cross-section.

3. The process of claim 2 further including the step of clamping the wound filament against the said forming bar.

4. Process of claim 1 wherein the stress-strain curve of said oriented polymeric filament exhibits no yield point.

5. Process of claim 1 wherein the polymer from which said filament is made is an absorbable polymer.

6. Process of claim 5 wherein the absorbable polymer is a lactide/glycolide copolymer.

7. Process of claim 5 wherein the absorbable polymer is a 90/10, mol/mol, glycolide/lactide copolymer.

* * * * *